(12) United States Patent
Delgado Domingos Antunes Malcata et al.

(10) Patent No.: US 11,707,494 B2
(45) Date of Patent: Jul. 25, 2023

(54) PRE-FERMENTED SYMBIOTIC MATRIX BASED ON A CEREAL SUSPENSION WITH ENCAPSULATED PROBIOTICS, MANUFACTURE PROCESS AND CORRESPONDING UTILIZATION

(71) Applicant: 5ENSESINFOOD, S.A., Maia (PT)

(72) Inventors: Francisco Xavier Delgado Domingos Antunes Malcata, Oporto (PT); Ana Maria Pereira Gomes, Oporto (PT); Joana Mafalda Patricio De Oliveira Fernandes, Aguas Santas (PT); Maria Isabel Moreira Da Costa Franco, Ermesinde (PT)

(73) Assignee: 5ENSESINFOOD, S.A., Maia (PT)

( * ) Notice: Subject to any disclaimer, the term of this patent is extended or adjusted under 35 U.S.C. 154(b) by 592 days.

(21) Appl. No.: 16/421,266

(22) Filed: May 23, 2019

(65) Prior Publication Data

US 2019/0307814 A1 Oct. 10, 2019

Related U.S. Application Data

(63) Continuation-in-part of application No. 14/547,789, filed on Nov. 19, 2014, now abandoned, which is a continuation of application No. 12/444,429, filed as application No. PCT/PT2007/000042 on Oct. 4, 2007, now abandoned.

(30) Foreign Application Priority Data

Oct. 6, 2006 (PT) .................................. 103582

(51) Int. Cl.
| | |
|---|---|
| *A23L 7/104* | (2016.01) |
| *A61K 35/744* | (2015.01) |
| *A23L 7/10* | (2016.01) |
| *A23L 33/21* | (2016.01) |
| *A23L 33/135* | (2016.01) |
| *A61K 35/745* | (2015.01) |
| *A61K 35/00* | (2006.01) |

(52) U.S. Cl.
CPC ............ *A61K 35/744* (2013.01); *A23L 7/104* (2016.08); *A23L 7/115* (2016.08); *A23L 33/135* (2016.08); *A23L 33/21* (2016.08); *A61K 35/745* (2013.01); *A23V 2002/00* (2013.01); *A23Y 2220/00* (2013.01); *A23Y 2300/00* (2013.01); *A61K 2035/115* (2013.01)

(58) Field of Classification Search
CPC ............ A61K 2035/115; A61K 35/744; A61K 35/745; A23L 7/104; A23L 7/115; A23L 33/21; A23L 33/135
See application file for complete search history.

(56) References Cited

U.S. PATENT DOCUMENTS

| | | |
|---|---|---|
| 5,190,755 A | 3/1993 | Molin |
| 5,554,520 A * | 9/1996 | Fowler .................... C12N 15/52 |
| | | 435/165 |
| 5,879,729 A | 3/1999 | King |
| 5,968,569 A | 10/1999 | Cavadini |
| 6,060,050 A | 5/2000 | Brown |
| 6,500,463 B1 | 12/2002 | Van Lengerich |
| 6,555,003 B2 * | 4/2003 | Ferro .......................... C02F 1/44 |
| | | 210/632 |
| 6,652,895 B2 | 11/2003 | Porzio |
| 6,783,780 B1 | 8/2004 | De Jong |
| 2001/0016220 A1 | 8/2001 | Jager |
| 2003/0170370 A1 | 9/2003 | Evenson |
| 2004/0023360 A1 | 2/2004 | Lacroix |
| 2004/0115308 A1 | 6/2004 | Bengtsson-Riveros |
| 2004/0175460 A1 | 9/2004 | Zenovich |
| 2005/0079244 A1 | 4/2005 | Giffard |
| 2005/0112111 A1 | 5/2005 | Marshall |

(Continued)

FOREIGN PATENT DOCUMENTS

| | | |
|---|---|---|
| AU | 687253 B2 | 2/1998 |
| CA | 2383021 A1 | 10/2002 |

(Continued)

OTHER PUBLICATIONS

Makarova et al., "Comparative genomics of the lactic acid bacteria", PNAS, 2006, vol. 103, No. 42, pp. 15611-15616.
Schell et al., "The genome sequence of Bifidobacterium longum reflects its adaptation to the human gastrointestinal tract", PNAS, 2002, vol. 99, No. 22, pp. 14422-14427.
Jung, KR 2001103110, 2001, Derwent.

*Primary Examiner* — W A Moore
(74) *Attorney, Agent, or Firm* — Lucas & Mercanti, LLP

(57) ABSTRACT

A pre-fermented symbiotic matrix based on a cereal suspension containing encapsulated probiotics and prebiotics, the manufacturing process and the corresponding use are disclosed. The invention complements the actual functional food market solving problems inherent to reduced shelf-life of foods due to loss of probiotic viability to values below the minimum limits needed to promote biological activity. The invention also improves the enzymatic process in the preparation of the cereal base and the fermentative process conditions at different levels, namely the ability to control the concentration of sugars in the cereal suspension without adding sugars, increase protein and fiber content, reduce fermentation time to reduce energy consumption during the process and reduce the risk of contamination as well as promote long term microbial stability maintenance. The invention is designed for cases where intolerance and/or allergy to dairy products occur, as wells for the pharmaceutical, cosmetic and food industries, including pet food.

14 Claims, No Drawings

(56) References Cited

U.S. PATENT DOCUMENTS

| | | | |
|---|---|---|---|
| 2005/0153018 A1 | 7/2005 | Ubbink | |
| 2006/0099321 A1 | 5/2006 | Sievert | |
| 2006/0154350 A1 | 7/2006 | Kolbakov | |
| 2009/0311376 A1* | 12/2009 | Rao | A23L 7/115 |
| | | | 426/28 |
| 2015/0071891 A1* | 3/2015 | Delgado Domingos Antunes Malcata | A61K 35/745 |
| | | | 424/93.45 |
| 2016/0249663 A1* | 9/2016 | Rajakaruna | A23L 33/22 |
| | | | 424/779 |
| 2018/0146699 A1* | 5/2018 | Vafeiadi | A23G 3/366 |
| 2019/0246676 A1* | 8/2019 | Bassi | A23J 3/30 |

FOREIGN PATENT DOCUMENTS

| | | | |
|---|---|---|---|
| EP | 0862863 | A2 | 9/1998 |
| WO | 9117672 | A1 | 11/1991 |
| WO | 9608261 | A1 | 3/1996 |
| WO | 0115714 | A1 | 3/2001 |
| WO | 2004037191 | A2 | 5/2004 |
| WO | 2005002367 | A1 | 1/2005 |
| WO | 2006007463 | A1 | 1/2006 |

* cited by examiner

PRE-FERMENTED SYMBIOTIC MATRIX BASED ON A CEREAL SUSPENSION WITH ENCAPSULATED PROBIOTICS, MANUFACTURE PROCESS AND CORRESPONDING UTILIZATION

CROSS REFERENCE TO RELATED APPLICATION

This Application is a continuation-in-part of U.S. application Ser. No. 14/547,789, filed Nov. 19, 2014, which is a continuation of U.S. application Ser. No. 12/444,429, filed Apr. 6, 2009, which is a 371 of PCT/PT2007/000042 filed Oct. 4, 2007, which claims priority of Portuguese Application No. PT 103582 filed Oct. 6, 2006, the contents of each of which are incorporated herein by reference.

FIELD OF INVENTION

The present invention is related with the manufacture of a pre-fermented symbiotic matrix, containing prebiotics and/or probiotics, and it is applicable to the pharmaceutical, cosmetic and preferably food industries, including pet food. The pre-fermented symbiotic matrix, free or not of dairy ingredients, applies to all populations, in particular to those elements with intolerance and/or allergy to dairy products.

Over the last few decades, detailed knowledge on the influence of diet on human health has increased greatly, and populations across the world have become conscious of the need for a so-called "healthy diet", justified by the life expectancy increases as well as representing an important public health issue. With the increasing popularity of probiotic products among consumers, food companies need to face the call for the manufacture of such products in order to appropriately meet constant market requests. All food is functional, in the general meaning of the term, insofar as they supply energy and nutrients necessary toward growth and maintenance. A food ingredient is considered as functional if it has been clearly demonstrated and scientifically validated, in an efficient scientific way that it beneficially affects health, beyond the classical nutritional effect associated therewith.

This market is characterized by being dynamic and innovative with a market quota of 10 to 15% and a growth rate of 20 to 30% per year, at world level.

Probiotics can be defined as viable microorganisms that affect the host beneficially in as much as they promote the balance of its intestinal bacterial ecosystem. *Lactobacillus*, *Bifidobacterium* and *Enterococcus*, genera considered potentially probiotic, offer a protection to the host against infections, considering that they prevent the attack, setting, response and/or virulence of specific enteropathogenics (antimicrobial activity). These probiotics also have a beneficial effect in the control of diarrhoeas, as well as in the reduction of the risk of development of some forms of cancer (anticarcinogenic activity). An effect on reduction levels of blood cholesterol (hypocholesterolaemic activity) is also described. Another possible effect, which has been scientifically validated, is the effect on the digestion of lactose, through the production of lactase (β-galactosidase) which facilitates the digestion of this sugar and offers solutions for individuals intolerant to lactose. The probiotic products' beneficial effect is secured when these contain a minimum of $10^6$ CFU/ml, which is in agreement with the assumption of a minimum therapeutic dose per day suggested to be $10^8$ to $10^9$ viable cells, which may be realisable through an intake of approximately 100 grams of product containing $10^6$-$10^7$ viable cells per millilitre or gram. Probiotics present natural limitations to their health benefits, due to their susceptibility to certain technological and functional factors, for instance high levels of oxygen, acid environments, freezing and the passage through the gastrointestinal tract.

Methods of encapsulation have begun to be applied, as a means to increase the survival rate of probiotics, through their protection from abovementioned adverse conditions. Microencapsulation is the technology of packing solids, liquids or gases in very small capsules, capable of releasing their content at controlled rates and under specific conditions.

Several microencapsulating techniques are available, viz. emulsion and spray-drying. Emulsion encapsulation consists on adding a small volume of solution containing microbial cells and polymers (discontinuous phase) to a greater volume of vegetable oil (continuous phase). This mixture is then homogenized forming a water-in-oil emulsion. Once obtained, the water-soluble polymer must be insolubilized via a saline solution with the objective of creating small gel particles in the oil phase. The size of the capsules can be controlled by varying the type of stirring and its speed as well as the saline solution addition mechanism. The process of emulsion encapsulation is easily scaled-up and leads great survival rates of microorganisms (80 to 95%). The resulting capsules present various sizes, which range from 25 µm to 50 µm.

On the other hand, the spray-drying method consists on drying an aqueous encapsulating agent mixture with viable microbial cells, using an atomizer. The drying occurs when the solution, after being vaporized, comes in contact with a hot air flow (entry temperature), and is subsequently, with the aid of a vacuum, gathered in the appropriate recipient. This technology has as greatest advantages the low cost of the procedure, the easiness of the operation, the possibility of using thermo-sensitive functional ingredients, the high quality/stability of the capsules obtained and the easy production in large quantities. The obtained capsules can vary in size between 5 and 75 µm.

A prebiotic is by definition a non-digestible food ingredient which positively affects the host, stimulating selectively the growth and/or activity of one or a limited number of bacteria in the colon.

The term symbiotic refers to a synergistic association of pre- and probiotic agents with physiological activity in the same food.

Presently, prebiotics and their combination with probiotics in an encapsulated form consist in an investment for food industry, with the intention of maintaining their long term stability and optimizing the nutritional qualities of the associated product.

The document US2001/0016220 lists components of food products, which contain biological active ingredients that may be encapsulated, as well as the process for their production and utilization. The components mentioned in this document comprise plant fibres including the ones proceeding from oats, soluble and insoluble polysaccharides, pectins, lenhins and gums. The biologically active components in the mentioned plant fibres may be probiotic microorganisms, prebiotics, enzymes, nutrients, secondary metabolites, natural or synthetic, substances with antioxidant activity, etc. The substances of encapsulation may be constituted by polysaccharides (of plant or microbial origin), emulsifiers, peptides, proteins and prebiotic substances.

In terms of the process of attainment of these components, the document in question foresees the introduction of biological active components into an environment that contains substances that form the capsules. Even though this document describes products based on cereals containing biologically active components, such as probiotics and/or prebiotics, encapsulated in a matrix formed by the plant fibres of the cereals, it differs considerably from the present invention, since this describes an aqueous suspension of pre-fermented cereals, with posterior encapsulation of microorganisms, by emulsion, fluidized bed, or by drying and subsequent addition of prebiotic components. In other words, in the previous document, all the components, prebiotics or probiotics, are encapsulated and are introduced in the matrix at the same phase, while this invention describes a process of attainment of these components in several phases, with protection of microbial activity through the encapsulation of microorganisms.

The document WO2005.002367 reports products and therapeutical compositions made of oats free of probiotic microorganisms, including proteins, hydrolysed proteins and emulsifying lipids. Besides that, the products and compositions may still include β-glucans, and plant sterols. The corresponding production process is carried out via an enzymatic treatment of the oats fraction for removal of the carbohydrates (preferentially by hydrolysis).

The document WO 02/065855 mentions non dairy products, made of cereal dispersions, containing β-glucans, proteins, natural sugars and proteins. The process to obtain such products uses enzymes, particularly hydrolases, as well as isomerases, applied to cereal suspensions.

The document WO 02/37984 reports products leavened by microbial cultures based on oat suspensions, free of soy and milk, as well as the corresponding manufacture. This document foresees the use of Lactobacillus and Streptococcus strains in the fermentation of the oat suspension, as well as the inclusion of several components, such as calcium hydrogeno-phosphate and/or calcium phosphate, β-glucan, maltose, maltodextrin, proteins, etc in an aqueous oat suspension which is later incubated for fermentation.

The document WO00/65930 reports products made of cereals, particularly oats, for further utilization as raw material in the food industry. The process of attainment of these products includes the preparation of a suspension, from bran, flakes or flour of cereals. This suspension is later homogenized, at a predetermined temperature and pressure, in order to obtain an emulsion. Afterwards, the emulsion can be leavened by microorganisms, such as Lactobacillus and Bifidobacterium, among others, acidified and finally pasteurized, (or even presented as a powder).

The document CA2383021 describes symbiotic compositions departing from β-glucans produced from cereals, obtained from flours or extracts of cereals, inoculated by bacteria for fermentation. Lactobacillus, Streptococcus and/or Bifidobacterium are inoculated in aqueous suspensions of cereals, treated with α-amylases, and added with a stabilizing agent.

The document WO2004/037191 describes symbiotic products, in liquid or frozen form, derived from soy or dairy products, composed of a mixture of probiotic components (e.g. Lactobacillus and Bifidobacterium) and prebiotics, in which these may be constituted by polymers, particularly, inulin or oligofructose. The process of manufacture thereof uses a mixture of prebiotic and probiotic components in a liquid phase; fermentation of this mixture occurs until pH reaches 4,5; and final blend leads to the final product. At this final stage, it is, still possible to include a percentage of carbon dioxide.

BRIEF SUMMARY OF THE INVENTION

The present invention's object is the development of a cereal symbiotic matrix, oat preferably, pre-fermented with encapsulated probiotics and free and/or encapsulated prebiotics, with the purpose of complementing the actual functional food market and solving problems inherent to the reduced shelf-life period of these foods. Moreover, the present invention's object is to improve both the enzymatic process in the preparation of the cereal base and the fermentative process conditions at different levels, namely the ability to control the concentration of sugars in the cereal suspension without adding external sugars, increased protein and fiber content, the fermentative process conditions at different levels, namely reduction of fermentation time as a means to economize energy during the manufacturing process, to reduce the risk of contamination and to maintain long term microbial stability.

The content described in the six aforementioned documents, differs substantially from the content of our invention, since they describe the fermentation of oat suspensions, with the addition of free microorganisms or enzymes, in just one phase, and may eventually include other additional components, while the invention under analysis describes suspensions of cereals pre-fermented by immobilized microorganisms, to which encapsulated probiotics and free or encapsulated prebiotics are subsequently added.

When the microorganisms are used in the free form the shelf-life of the final product is reduced and the stability/viability of microorganisms over the storage period as well as in their passage through the gastro-intestinal tract is diminished, in comparison to the symbiotic pre-fermented matrix with encapsulated probiotics (increase of 40 to 60%), object of the present invention.

This present solution also solves the problems associated with reduced shelf-life mentioned in patents WO 02/37984, WO 00/65930, CA2383021, WO 2004/037191 (an increase of 40 to 60% compared to the existing products with free microorganisms is reported) and maintains long term microbial stability.

The document EP 0 862 863 A2 has for object of invention the development of dried extruded cereals with surface and/or enclosed microorganisms, and with soluble fibre sources listing as examples of application breakfast cereals and animal feed. The object of invention foresees the development of a cereal symbiotic matrix, preferentially in oatmeal, pre-fermented with encapsulated probiotics and free and/or encapsulated prebiotics, which, when applied together, will confer a stabilizing effect on the microorganisms present in the final product and favour the passage through the gastro-intestinal tract. Furthermore, an additional object of this invention is the health claim of cholesterol reduction associated to β-glucan, as a source of non-digestible prebiotic soluble fibres. The cereal suspension, preferentially oatmeal, is presented in fresh, lyophilized, and frozen forms, adapted to the needs of the intervening parts in the food chain, and hence with several applications in the food industry.

The document WO2004.070026 discloses continuous processes concerning yeast immobilization in K-carrageenan or alginate gel spheres, e.g. in beer production, through formation of an emulsion e.g. with the continuous non-aqueous phase (plant oil) and the disperse aqueous phase (inoculated K-carrageenan with yeast), using static stirrers. This subject differs from that disclosed in the present invention, because the immobilization process described, although pertaining to an emulsion between a plant oil and a microorganism-inoculated polymer, encompasses a yeast, whereas those in the present invention are all of probiotic microorganisms.

The conceptualization of a phased process, to obtain symbiotic products, from pre-fermented cereal suspensions with added encapsulated probiotics, and subsequent incorporation of prebiotic compounds in the cereal matrix leads to a superior product, not only from a nutritional point of view, due to long term microbiological stability maintenance, but also in what concerns organoleptic properties.

DETAILED DESCRIPTION OF THE INVENTION

The present invention reports a cereal symbiotic matrix, preferentially oatmeal, pre-fermented with encapsulated probiotic and prebiotic compounds, its process of manufacture and its use in several applications, especially in the food industry but also in the pharmaceutical industry or similar counterparts.

The products obtained possess organoleptic characteristics that are identical to those produced by traditional fermentation processes.

When encapsulated microorganisms are included, these products also have the advantage of increasing their viability/stability, either as a long shelf-life or during passage through the gastro-intestinal tract following ingestion.

The matrices also present, as an additional advantage, an extended expiration date up to 40% to 60% higher than those presented by available products on the market.

Through the use of this technology one obtains a pre-fermented product with residual quantities of free microorganisms and with the same organoleptic characteristics as those of a traditionally fermented product, being therefore a more valued product.

The immobilization technique of microbial cells confers advantages in comparison to free cell systems, such as: (i) reduction in fermentation time up to 50 to 60%; (ii) increase of the microbial metabolism and stability; (iii) reduced risk of contamination; (iv) higher cell density; (v) stable product quality associated with a decrease of post-acidification risk due to probiotic action, for example; (vi) improved substrate use and (vii) long time cell reutilization due to constant cellular regeneration.

The process of obtaining these products reveals a method for improvement of the fermentative process conditions at several levels such as, (i) continuous reutilization of the immobilized cells; (ii) fermentation time reduction contributes to energy saving throughout the process, (iii) reduction of contaminating risks and (iv) long term maintenance of microbial stability.

1. Preparation process of oatmeal suspension (concentrate of 5-50% (w/w)
    1.1. mixture of flakes, bran and/or flour in water at temperatures ranging from 80-100° C. until achieving starch gelatinization;
    1.2. liquefaction using α-amylases (of bacterial or fungi origin) at temperatures controlled between 50° C. and 90° C., pH between 6 and 8;
    1.3. saccharification of liquefied oat content using glucoamylases at temperatures controlled between 50° C. and 90° C., pH between 6 and 8;
    1.4. solubilisation using a glutaminase at temperatures controlled between 40 and 60° C.; or using a soluble salt such as sodium bicarbonate or sodium hydroxide;
    1.5. filtration of the obtained suspension;
    1.6. cooling of the mixture until a range of temperatures between 25 and 48° C.

In one embodiment, the water to be used in step 1.1 is previously obtained through an osmosis process in order to standardize the flavour of the final product by removing the minerals that may cause off-flavours.

The entire enzymatic process occurs in a tank during 65 minutes after starch gelatinization performed during the first 15 minutes at 90° C., leading to a process with a total duration of up to 80 minutes.

In one embodiment, the enzymatic process described above ends when sugar content, in terms of glucose, achieves 150 g/L and 25±5° Brix.

The enzymes used in the process described in the present patent application are introduced at the same stage according to a sequential addition respecting the function of each enzymes, viz.—BAN 480 L (α-amylase), AMG 300 L (glucoamylase) and glutaminase. All the enzymes were obtained commercially from NOVOZYMES.

Having an enzyme (glutaminase) and/or salts (sodium bicarbonate) allow to control protein precipitation caused by the pH.

In a particular embodiment, the α-amylase is used on a concentration between 0.01% and 2% of cereal concentration, glucoamylase is used on a concentration between 0.01% and 1% of cereal concentration and glutaminase is used on a concentration between 0.01% and 1% of cereal concentration.

The above-mentioned steps have the advantage of allowing a higher concentration of the cereal to be introduced in the process, leading to commercial products with a cereal concentration up to 50% (w/w). This implies a higher content of protein and fiber due to the high cereal concentration. The steps described above also lead to an increased content of starches and carbohydrates, which are the substrate for the enzymatic process, which in turn leads to an increase of glucose and other oligosaccharides. The high concentration of sugars in the oat base to be fermented, leads to a higher bioavailability of oligosaccharides and simple sugars for the fermentative action of the microorganisms (which require a given content of sugars). This also allows to decrease the addition of the inoculum to a minimum of 0.1% (m/v). This way, the final product will not require any added sugars, which in turn makes the product more appealing to the consumer.

Additionally, the liquefaction step, also enables the standardization of cereal viscosity values (<500 Cp) for industrial production.

2. Process of pre-fermentation in fluidized bed reactor associated with cell encapsulation by emulsion
    2.1. Process of pre-fermentation
        The process of pre-fermentation is performed in a fluidized bed reactor with immobilized microorganisms by cells obtained in steps 2.1.1. through 2.4.3.
        The capsules are introduced in a column, with porosity smaller than the diameter of the capsules to induce the microorganisms-matrix interaction, inside the pressurized reactor with constant and controlled bi-directional nitrogen flow. The immobilized cells inside the column are reutilized in the fermentation process until they lose their metabolic properties.
        2.1.1. Cell culture preparation
        2.1.1.1. Preparation of the inocula from frozen cultures and consequent activation by two consecutive transfers in MRS Broth supplemented with L-cysteine-HCl 0.05% (w/v).
        2.1.1.2. Inoculation of 1 to 20% (v/v) in 1000 mL of MRS Broth (Man Rogosa and Sharpe) supplemented with L-cysteine-HCl 0.05% (m/v) and subsequent incubation for 24 h at 37° C., under anaerobic conditions, for

*Lactobacillus acidophilus* Ki and 48 h at 37° C. under anaerobic conditions for *Bifidobacterium animalis* Bo and Bb12, for example.

2.1.1.3. Centrifugation of the resulting cultures at 4000 rpm for 15 minutes, at 4° C., subsequent washing of pellet with, for example, NaCl 0.9% (w/v) solution, and resuspension in 100 mL of the same solution.

2.2. Polymer solution preparation 2.2.1. Preparation of a polymer solution, for example, k-carrageenan 1 to 5% (w/v), with continuous stirring, variable duration between 1 to 4 hours, temperatures between 60 and 80° C., followed by cooling down to a temperature range of 35 to 45° C.

2.3. Oil solution preparation 2.3.1. Mixture of vegetable oil with one of the following compounds: Tween 80 0.2% (v/v) and/or a protective agent, as for a non-limiting example, laurel sodium sulphate 0.5% (v/v).

2.4. Capsule preparation 2.4.1. Mixture of cellular suspension 1 to 20% (v/v) (see 2.1.) with the polymer solution 1 to 5% (w/v) (see 2.2.).

2.4.2. Addition of the resulting mixture to 75 to 98% of the prepared oil solution (see 2.3.). The obtained solution is homogenised forming a water-in-oil emulsion.

2.4.3. The capsule formation occurs after the addition of a solution of KCl 10 mM, for example, to the mixture at a temperature range of 4 to 8° C.

2.5. Pre-fermentation process operation conditions

After attainment of the capsules with microorganisms for utilization in a fluidized bed reactor, the process of pre-fermentation is performed at a temperature between 20° C. to 52° C., during 4 to 8 hours, under sterile and anaerobic conditions (circulating nitrogen flux), resulting in a fermented matrix. This suspension is drained into the reactor where the incorporation of the remaining food ingredients occurs.

3. Microorganisms encapsulation process by emulsion and/or spray-drying

The microorganisms' encapsulation is done using the encapsulation techniques:

3.1. Emulsion, as described in point 2;

3.2. Spray-drying:

3.2.1. Preparation of a cellular suspension with polymers (see points 2.2; 2.2.1; and 2.4.1);

3.2.2. Drying of 250 ml of the previous mixture under the constant conditions of inlet and outlet temperatures of 150-175° C. and 50-85° C., respectively;

3.2.3. Addition of the resulting powder into the pre-fermented oat suspension (point 2.5) in a proportion of 2-5% (w/v), in a way to guarantee $10^8$-$10^{10}$ CFU in the matrix, per 100 g or 100 mL.

4. Food ingredients incorporation:

Addition of ingredients to the matrix obtained in the previous process (point 3.2.3,), having as an example inulin, at a concentration range between 1-3%, maintaining, as a non limitative example sea-salt, among others.

5. Presentation forms of the matrix

The pre-fermented symbiotic matrix based on an oat suspension with encapsulated probiotics can be presented either in a fresh form, lyophilized and/or frozen. The fresh matrix can be further presented either in gel or extruded form.

6. Microbiological/Shelf-life study

When encapsulated microorganisms are included, the products also have the advantage of increasing their viability, stability, either as a long shelf-life or during passage through the gastro-intestinal tract following ingestion. The fermented cereal product of the present patent application also presents an extended expiration date up to 40% to 60% higher than those presented by available products on the market.

Furthermore, the fermented symbiotic matrix is free from fermenting microorganisms and consequently post-acidification phenomenon does not occur, thereby increasing the shelf-life.

The advantage conferred by the invention is demonstrated by Table 1, where the ability to enhance the time of shelf-life is compared to a fermented product such as yogurt. By definition, shelf-life is the period during which the product maintains its microbiological safety and suitability at a specified storage temperature and, where appropriate, specified storage and handling conditions (see, e.g. Code of Hygienic Practice for Milk and Milk Products—CAC/RCP 57-2004).

Shelf life experiments with the fermented cereal product of the present application have been conducted in order to identify and compare the time that the product is stable and with the desired characteristics (microorganisms' quality in order to have beneficial effect on the final consumer).

The main goal of this study was to follow the overall product microbiology evolution of two different samples/microorganisms (*Lactobacillus acidophilus* and *Bifidobacterium lactis*): i) the behavior of the residual microorganisms on the cereal suspension, ii) the behavior of the barrier/passage between the cereal and the microorganisms inside the capsules and iii) their own behavior inside.

The medium used on this study was applied specifically to enumerate the microorganisms *Lactobacillus acidophilus* and *Bifidobacterium lactis*. The study range temperature used was to simulate the refrigeration temperature of the storage period on this kind of fermented product. The duration of the study and the sampling points were done to evaluate the product shelf-life and compare with similar fermented products.

At the end of the study, the capsules' sample with *Bifidobacterium lactis* had enough microorganisms' enumerations to guarantee the minimum biological beneficial effect at the ingestion of the fermented product (at least $10^8$-$10^{10}$ CFU/g). The sample with *Lactobacillus acidophilus* encapsulated can easily achieve the same doses on other productions because the level obtained of the inoculated microorganisms was similar ($10^7$ to $10^8$ CFU/g).

The report showed that the product obtained by the invention was suitable until, at least, 52 days which is a significantly higher duration than other regular commercial products, such as yogurt, which typically have a shelf-life of approximately 24 days. Thus, when compared with the shelf-life of the product obtained by the method of the invention the product indeed has 40-60% higher shelf life.

TABLE 1

Shelf-life - Microbiological study:
Data (results in CFU/g):

| Sample Name | Initial | Day 4 | Day 8 | Day 12 | Day 20 | Day 32 | Day 36 | Day 40 | Day 52 |
|---|---|---|---|---|---|---|---|---|---|
| *Lactobacillus* Capsule 1 | 2.7 e7 | 1.3 e7 | 2.4 e7 | 1.0 e7 | 1.0 e7 | 3.0 e7 | 2.2 e7 | 3.3 e7 | 6.5 e7 |
| Oat Slurry 1 | <100 | <100 | 600 | <100 | 3600 | 1000 | 1500 | <100 | <100 |
| *Bifidobacterium* Capsule 2 | 1.3 e8 | 1.2 e8 | 1.2 e8 | 1.1 e8 | 3.0 e8 | 1.0 e8 | 3.0 e8 | 2.0 e8 | 6.0 e8 |
| Oat Slurry 2 | 1400 | 3200 | 100 | 200 | 2400 | 700 | <100 | 200 | 900 |

*Lactobacillus* Capsule 1 - Capsules with microorganisms Genera *Lactobacillus*
Oat Slurry 1 - Oat suspension separated from capsules with microorganisms Genera *Lactobacillus*
*Bifidobacterium* Capsule 2 - Capsules with microorganisms Genera *Bifidobacterium*
Oat Slurry 2 - Oat suspension separated from capsules with microorganisms Genera *Bifidobacterium*

To study microorganisms's enumeration in MRS Agar supplemented with L-cysteine-HCl 0.05% (w/v) using spread technique to determine lactic count for the capsules and oat suspension. The product was stored at 4° C.-6° C. and analyzed at the following timepoints: initial, 4, 8, 12, 20, 32, 36, 40 and 52 days. The first decimal dilution was −2.

EXAMPLES

Example I

Oat concentrated base is obtained from 30% (w/w) oat bran aqueous extraction, which is submitted to an enzymatic treatment of partial hydrolysis and saccharification of starch, followed by a heat treatment.

Produced from dehulled, cleaned and heat stabilized oats by flaking and cleaning followed by milling.

Cereal Sources/Types:
Oat bran
Industrial Procedure:

In this example oat bran is dispersed using a blend table into a tank that contains hot water at 90° C. Water used to mixture oat bran is previously obtained through an osmosis process in order to standardize the flavour of final product through the removal of minerals that can cause off-flavours.

Oat dispersion is performed according to a factorial plan that involves percentage of cereal, enzymes concentration, time, temperature, sugar formation and Brix, according to the steps below.

The process comprises three main steps: liquefaction using α-amylases at optimal operation conditions namely temperatures between 50° C. and 70° C. at pH maintained between 6 and 8; saccharification using alfa-glucoamylases at optimal operation conditions namely 50° C.≤T≤70° C. at neutral pH; and oat solubilization using a glutaminase at optimal operation conditions namely 40° C.≤T≤60° C. at a pH maintained between 6 and 8.

For this example, the enzymes used are BAN 480 L at 0.30% of cereal concentration, AMG 300 L at 0.40% of cereal concentration and glutaminase at 0.10% of cereal concentration. All the enzymes are commercialized by NOVOZYMES.

The enzymes used are introduced at the same stage according to a sequential addition respecting the function of each enzymes, viz.—BAN 480 L, AMG 300 L and glutaminase.

The entire enzymatic process occurs in a tank during 65 minutes after starch gelatinization performed during the first 15 minutes at 90° C., reaching 80 minutes process.

The enzymatic process ends when sugar content, in terms of glucose, achieves 150 g/L and 25±5° Brix.

Decantation of oat slurry is applied when whole grain or bran is used in the formulation. Decantation can be omitted when insoluble fibers are considered a product specification.

Product resulted from decantation viz.—oat base can be submitted to a fermentation process according the present invention.

In this particularly example, the oat base/oat suspension is cooled from 70° C. to 43° C. through a heat exchanger. Fermentation is carried out into a jacketed tank with controlled pH, temperature and agitation (constant 50 rpm). Lactic acid bacteria (LAB) and bifidobacteria microorganisms are introduced by direct VAT into a tank with constant agitation together with isotonic solution to hydrate. The encapsulation process is performed with the addition of the polymer with oil and the inoculum together with the contact with $Ca_2Cl$ solution at 0.1 M to the capsule formation at 4 to 8° C. Capsules with YF L02, from CHR Hansen, are introduced at 0.10% inoculum to the fermenter tank, which leads to a 4 hours fermentation process, ending when pH of oat base is less than 4.55. After the fermentation there is a step of drain the base to continue the process ahead and the remain capsules stay at the fermenter in order to ferment the next round up to 3 times.

Enzymatic activity is eliminated by a direct steam injection unit which comprise the following steps: a) pre-heating of oat base up to 90° C., direct steam injection, sterilization binomial time and temperature (130° C. for 30 seconds), cooling process followed by aseptic filling.

The oat liquid prepared may be used as such or used as a basis for the preparation of different products with the addition of food ingredients namely encapsulated microorganisms.

According with this example, the final product (symbiotic matrix) has the following tables (2, 3 and 4) with physic-chemical, organoleptic and microbiological characteristics:

TABLE 2

PHYSICAL AND CHEMICAL CHARACTERISTICS
Tolerances can be applied due to raw material natural variability.

| Characteristic | Method | Unit | Target | Minimum | Maximum | Tolerance |
|---|---|---|---|---|---|---|
| pH | Potentiometer | pH unit | 4.55 | 4.0 | 6.5 | n.a. |
| Brix | Refractometer | °Brix | 25.0 | 20.0 | 30.0 | n.a. |
| Dry Matter Content | Oven (105° C., constant weight) | % (w/w) | 27.0 | 22.0 | 32.0 | ±5 |
| Glucose (rapid method) | Glucometer (dilution 1\|300) | g/l | 120 | 80 | 200 | n.a. |
| Protein | (F = 6.25) | % (w/w) | 3.0 | 2.5 | 5.0 | n.a |
| Viscosity | Brookfield (20° C., RPM, spindle) | cP | n.a. | n.a. | <500 | n.a. |

TABLE 3

ORGANOLEPTICAL CHARACTERISTICS

| | |
|---|---|
| Direct Inspection/Aspect | Homogeneous product with characteristic appearance, color and smell. No dark specks or any other type of visual defects. |
| Color | Yellowish, without brown or strange colors. |
| Odor | Characteristic to cereal, without strange odors. |
| Taste | Characteristic to cereal, sweet, without off-flavors. |
| Mouthfeel | With a certain viscosity, non-watery sensation. |

TABLE 4

MICROBIOLOGICAL CHARACTERISTICS

| CFU/g | Target* |
|---|---|
| Total viable count at 30° C. | Absence in 50 g |
| Yeasts | Absence in 50 g |
| Moulds | Absence in 50 g |
| Spore forming bacteria | Absence in 50 g |
| LAB and *Bifidobacteria* (YF-L02) | $10^6$ to $10^7$ |

Example II

Oat concentrated base is obtained from 40% (w/w) whole grain oat flour aqueous extraction, which is submitted to an enzymatic treatment of partial hydrolysis and saccharification of starch, followed by a heat treatment. Produced from dehulled, cleaned and heat stabilized oats by flaking and cleaning followed by milling.

Cereal Sources/Types:
Whole grain oat flour
Industrial Procedure:

In this example oat bran is dispersed using a blend table into a tank that contains hot water at 90° C. Water used to mixture oat bran is previously obtained through an osmosis process in order to standardize the flavour of final product through the removal of minerals that can cause off-flavours.

Oat dispersion is performed according to a factorial plan that involves percentage of cereal, enzymes concentration, time, temperature, sugar formation and Brix, according to the steps below.

The process comprises three main steps: liquefaction using α-amylases at optimal operation conditions namely temperatures between 70° C. and 90° C. at pH maintained between 6 and 8; saccharification using α-glucoamylases at optimal operation conditions namely 50° C. T 70° C. at neutral pH; and oat solubilization using a soluble salt, for example, sodium bicarbonate at 0.15% (w/v).

For this example, the enzymes used are TERMAMYL at 0.90% of cereal concentration and AMG 300 L at 0.30% of cereal concentration. All the enzymes are commercialized by NOVOZYMES.

The enzymes used are introduced at the same stage according to a sequential addition respecting the function of each enzymes, viz. —TERMAMYL and AMG 300 L.

The entire enzymatic process occurs in a tank during 45 minutes after starch gelatinization performed during the first 35 minutes at 90° C., reaching 80 minutes process.

The enzymatic process ends when sugar content, in terms of glucose, achieves 150 g/L and 30±5° Brix.

Decantation of oat slurry is applied when whole grain is used in the formulation. Decantation can be omitted when insoluble fibers are considered a product specification.

Product resulted from decantation viz.—oat base can be submitted to a fermentation process according the present invention.

In this particularly example, the oat base/oat suspension is cooled from 70° C. to 43° C. through a heat exchanger. Fermentation is carried out into a jacketed tank with controlled pH, temperature and agitation (constant 50 rpm). Bifidobacteria microorganisms are introduced by direct VAT into a tank with constant agitation together with isotonic solution to hydrate. The encapsulation process is performed with the addition of the polymer with oil and the inoculum together with the contact with $Ca_2Cl$ solution at 0.1 M to the capsule formation at 4 to 8° C. Capsules with Nu-trish® BY-01 DA, from CHR Hansen, are introduced at 0.10% inoculum to the fermenter tank, which leads to a 4 hours fermentation process, ending when pH of oat base is less than 4.55. After the fermentation there is a step of drain the base to continue the process ahead and the remain capsules stay at the fermenter in order to ferment the next round until 3 times. The capsules are reused at least three times in the next fermentation processes.

Enzymatic activity is eliminated by a direct steam injection unit which comprise the following steps: a) pre-heating of oat base up to 90° C., direct steam injection, sterilization binomial time and temperature (130° C. for 30 seconds), cooling process followed by aseptic filling.

The oat liquid prepared may be used as such or used as a basis for the preparation of different products with the addition of food ingredients namely encapsulated microorganisms.

According with this example, the final product (symbiotic matrix) has the following tables (5, 6 and 7) with physic-chemical, organoleptic and microbiological characteristics:

TABLE 5

PHYSICAL AND CHEMICAL CHARACTERISTICS
Tolerances can be applied due to raw material natural variability.

| Characteristic | Method | Unit | Target | Minimum | Maximum | Tolerance |
|---|---|---|---|---|---|---|
| pH | Potentiometer | pH unit | 4.55 | 4.0 | 6.5 | n.a. |
| Brix | Refractometer | °Brix | 35.0 | 30.0 | 40.0 | n.a. |
| Dry Matter Content | Oven (105° C., constant weight) | % (w/w) | 37.0 | 32.0 | 42.0 | ±5 |
| Glucose (rapid method) | Glucometer (dilution 1|300) | g/l | 120 | 80 | 200 | n.a. |
| Protein | (F = 6.25) | % (w/w) | 3.0 | 2.5 | 5.0 | n.a |
| Viscosity | Brookfield (20° C., RPM, spindle) | cP | n.a. | n.a. | <500 | n.a. |

TABLE 6

ORGANOLEPTICAL CHARACTERISTICS

| Direct Inspection/ Aspect | Homogeneous product with characteristic appearance, color and smell. No dark specks or any other type of visual defects. |
|---|---|
| Color | Yellowish, without brown or strange colors. |
| Odor | Characteristic to cereal, without strange odors. |
| Taste | Characteristic to cereal, sweet, without off-flavors. |
| Mouthfeel | With a certain viscosity, non-watery sensation. |

TABLE 7

MICROBIOLOGICAL CHARACTERISTICS

| CFU/g | Target* |
|---|---|
| Total viable count at 30° C. | Absence in 50 g |
| Yeasts | Absence in 50 g |
| Moulds | Absence in 50 g |
| Spore forming bacteria | Absence in 50 g |
| *Bifidobacteria* (nu-trish ® BY-01 DA) | $10^6$ to $10^7$ |

DESCRIPTION OF EMBODIMENTS

Now, preferred embodiments of the present application will be described in detail.

The present patent application describes a process of obtaining a fermented cereal product comprising the following steps:

Preparation process of cereal suspension with a concentration between 5 to 50% (w/w), wherein the preparation step comprises the mixture cereals in water at temperature between 80° C. and 100° C.; liquefaction using α-amylases at temperatures controlled between 50° C. and 90° C. and pH between 6 and 8; saccharification of the liquefied content using glucoamylases at temperatures controlled between 50° C. and 90° C. and pH between 6 and 8; and solubilisation using glutaminase at temperatures controlled between 40 and 60° C. or using a soluble salt such as sodium bicarbonate or sodium hydroxide.

Adding macroencapsulated immobilized probiotic or non-probiotic microorganisms to the cereal suspension prepared on the previous step, such that said microorganisms ferment the cereals and generate an aqueous suspension containing (i) fermented cereal suspension and (ii) macroencapsulated immobilized probiotic or non-probiotic microorganisms;

Separating the aqueous suspension generated in the previous step from the macroencapsulated immobilized probiotic or non-probiotic microorganisms, to obtain an aqueous fermented cereal suspension without the macroencapsulated immobilized probiotic or non-probiotic microorganisms; and Incorporating into the aqueous fermented cereal suspension without the macroencapsulated immobilized probiotic or non-probiotic microorganisms obtained in the previous step, at least on other component selected from the group consisting of:
Free or encapsulated prebiotics;
Free or microencapsulated probiotic or non-probiotic microorganisms;
Other food ingredients, free or encapsulated.

In one embodiment, the cereals are selected from flakes, bran or flour.

In one embodiment, the cereals include oats.

In another embodiment, the cereals are combined with at least one of:
One or more other cereals usually applied in food industry; or
One or more legumes.

In one embodiment, the water to be used in the first step is previously obtained through an osmosis process in order to standardize the flavour of the final product by removing the minerals that may cause off-flavours.

In one embodiment, the enzymatic process described above ends when sugar content, in terms of glucose, achieves at least 150 g/L and at least 25±5° Brix.

In a particular embodiment, the α-amylase is used on a concentration between 0.01% and 2% of cereal concentration, glucoamylase is used on a concentration between 0.01% and 1% of cereal concentration and glutaminase is used on a concentration between 0.01% and 1% of cereal concentration.

In one embodiment the fermented cereal product has residual quantities of free microorganisms, and comprises encapsulated prebiotics, free or microencapsulated probiotic or non-probiotic microorganisms, and other food ingredients selected from the group consisting of antioxidants, fatty acids, vitamins, minerals, sweeteners, flavors, fruit pulp and enzymes.

In one embodiment, the macroencapsulated immobilized probiotic or non-probiotic microorganisms are generally recognized as safe.

In one particular embodiment, the macroencapsulated immobilized probiotic or non-probiotic microorganisms are from the *Bifidobacterium* or *Lactobacillus* genera.

In one embodiment, the amount of free or microencapsulated probiotic or non-probiotic microorganisms incorporated into the above-described fermented cereal suspension is at least $10^8$-$10^{10}$ CFU/g.

In one embodiment, the macroencapsulated immobilized probiotic or non-probiotic microorganisms are encapsulated in a coating material selected from proteins, polysaccharides, lipids or hydrocolloids.

In one embodiment, the fermentation comprises placing a cereal suspension in a reactor with macroencapsulated immobilized probiotic or non-probiotic microorganisms.

The fermented cereal product obtained by the process described in the present patent application comprises:
- an aqueous fermented cereal suspension without macroencapsulated immobilized probiotic or non-probiotic microorganisms;
- at least one other component selected from a group consisting of:
  i. free or encapsulated prebiotics;
  ii. free or microencapsulated probiotics/non-probiotics; and
  iii. other food ingredients, free or encapsulated selected from the group consisting of antioxidants, fatty acids, vitamins, minerals, sweeteners, flavors, fruit pulp and enzymes;
- a glucose concentration of at least 150 g/L and at least 25±5° Brix.

In one embodiment, the fermented cereal product has a water activity (aw) of at least 0.3.

In one embodiment, said prebiotics comprise β-glucan soluble fiber, in biologically active quantities, preferably extracted from cereals or legumes. In a preferable embodiment, said prebiotics comprise a minimum of 0.75% (w/w) of β-glucan soluble fiber.

In one embodiment, apart from β-glucan soluble fibres, other prebiotic compounds such as, non limiting examples, inulin, fructooligossacharides (FOS) and chitosans.

A fermented cereal product, characterised by allowing the integration of other food ingredients, that apart from the prebiotic function can still allow for other functions, such as, non limiting, organoleptic functions (such as, non limiting, sweeteners, flavours and/or fruit pulp) and texture (such as enzymes).

Additional embodiments according to the invention are provided below:

Embodiment 1 is process of obtaining a fermented cereal product by carrying out the following steps:
- preparation process of cereal suspension with a cereal concentration between 5 to 50% (w/w), wherein the preparation step comprises the mixture cereals in water at temperature between 80° C. and 100° C.; liquefaction using α-amylases at temperatures controlled between 50° C. and 90° C. and pH between 6 and 8; saccharification of the liquefied content using glucoamylases at temperatures controlled between 50° C. and 90° C. and pH between 6 and 8; and solubilisation using glutaminase at temperatures controlled between 40 and 60° C. or using a soluble salt such as sodium bicarbonate or sodium hydroxide;
- adding macroencapsulated immobilized probiotic or non-probiotic microorganisms to the cereal suspension prepared on the previous step, such that said microorganisms ferment the cereals and generate an aqueous suspension containing (i) fermented cereal suspension and (ii) macroencapsulated immobilized probiotic or non-probiotic microorganisms;
- separating the aqueous suspension generated in the previous step from the macroencapsulated immobilized probiotic or non-probiotic microorganisms, to obtain an aqueous fermented cereal suspension without the macroencapsulated immobilized probiotic or non-probiotic microorganisms; and
- Incorporating into the aqueous fermented cereal suspension without the macroencapsulated immobilized probiotic or non-probiotic microorganisms obtained in the previous step, at least on other component selected from the group consisting of:
  Free or encapsulated prebiotics;
  Free or microencapsulated probiotic or non-probiotic microorganisms;
  Other food ingredients, free or encapsulated.

Embodiment 2 is a process of obtaining a fermented cereal product according to embodiment 1, in which the cereals are selected from flakes, bran or flour.

Embodiment 3 is a process of obtaining a fermented cereal product according to embodiment 1, in which the cereals include oats.

Embodiment 4 is a process of obtaining a fermented cereal product according to embodiment 1, in which the cereals are combined with at least one of:
  One or more other cereals usually applied in food industry; or
  One or more legumes.

Embodiment 5 is a process of obtaining a fermented cereal product according to embodiment 1, in which the water to be used in the first step is previously obtained through an osmosis process in order to standardize the flavour of the final product by removing the minerals that may cause off-flavours.

Embodiment 6 is a process of obtaining a fermented cereal product according to embodiment 1, in which the enzymatic process described above ends when sugar content, in terms of glucose, achieves at least 150 g/L and at least 25±5° Brix.

Embodiment 7 is a process of obtaining a fermented cereal product according to embodiment 1, in which the α-amylase is used on a concentration between 0.01% and 2% of cereal concentration, glucoamylase is used on a concentration between 0.01% and 1% of cereal concentration and glutaminase is used on a concentration between 0.01% and 1% of cereal concentration.

Embodiment 8 is a process of obtaining a fermented cereal product according to embodiment 1, wherein the macroencapsulated immobilized probiotic or non-probiotic microorganisms are generally recognized as safe.

Embodiment 9 is a process of obtaining a fermented cereal product according to embodiment 1, wherein the macroencapsulated immobilized probiotic or non-probiotic microorganisms are from the *Bifidobacterium* or *Lactobacillus* genera.

Embodiment 10 is a process of obtaining a fermented cereal product according to embodiment 1, in which the amount of free or microencapsulated probiotic or non-probiotic microorganisms incorporated into the above-described fermented cereal suspension is at least $10^8$-$10^{10}$ CFU/g.

Embodiment 11 is a process of obtaining a fermented cereal product according to embodiment 1, in which the macroencapsulated immobilized probiotic or non-probiotic microorganisms are encapsulated in a coating material that ca be proteins, polysaccharides, lipids or hydrocolloids.

Embodiment 12 is a process of obtaining a fermented cereal product according to embodiment 1, where the fermentation includes the placing of a cereal suspension in a reactor with macroencapsulated immobilized probiotic or non-probiotic microorganisms.

Embodiment 13 is a fermented cereal product obtained according to process described in embodiment 1, which includes:
- an aqueous fermented cereal suspension without macroencapsulated immobilized probiotic or non-probiotic microorganisms;
- at least one other component selected from a group consisting of:
  i. free or encapsulated prebiotics;
  ii. free or microencapsulated probiotics/non-probiotics; and
  iii. other food ingredients, free or encapsulated selected from the group consisting of antioxidants, fatty acids, vitamins, minerals, sweeteners, flavors, fruit pulp and enzymes;
- a glucose concentration of at least 150 g/L and at least 25±5° Brix.

Embodiment 14 is a fermented cereal product according to embodiment 13, wherein said prebiotics includes β-glucan soluble fiber, in biologically active quantities, preferably extracted from cereals or legumes. In a preferable embodiment, said prebiotics comprise a minimum of 0.75% (w/w) of β-glucan soluble fiber.

Embodiment 15 is a fermented cereal product according to embodiment 14, wherein apart from β-glucan soluble fibres, other prebiotic compounds such as, inulin, fructooligossacharides (FOS) and chitosans are included.

The invention claimed is:

1. A process of obtaining a fermented cereal product consisting of:
   preparing a cereal suspension with a cereal concentration between 5 to 50% (w/w), by mixing cereals in water at a temperature between 80° C. and 100° C.;
   carrying out liquefaction using α-amylases at temperatures controlled between 50° C. and 90° C. and pH between 6 and 8;
   carrying out saccharification of the liquefied content using glucoamylases at temperatures controlled between 50° C. and 90° C. and pH between 6 and 8;
   solubilizing using glutaminase at temperatures controlled between 40 and 60° C., or solubilizing using a soluble salt to obtain a suspension;
   carrying out filtration of the suspension and cooling until a range of temperature between 25° C. and 48° C. is reached thereby obtaining the cereal suspension with the cereal concentration between 5 to 50% (w/w);
   preparing macroencapsulated immobilized probiotic or non-probiotic microorganisms by
      preparing a cell culture of microorganisms resuspended in sodium chloride solution thereby obtaining a cellular suspension;
      preparing a polymer solution with continuous stirring at temperatures between 60° C. and 80° C., followed by cooling down to a temperature range of 35° C. and 45° C.;
      preparing an oil solution using a mixture of vegetable oil with polysorbate 80 and/or a protective agent; and
      preparing capsules by mixing the cellular suspension with the polymer solution, adding the oil solution to obtain a homogenized water-in-oil emulsion, and adding a salt solution at a temperature range of 4° C. to 8° C. to form the macroencapsulated immobilized probiotic or non-probiotic microorganisms;
   adding the macroencapsulated immobilized probiotic or non-probiotic microorganisms to the cereal suspension prepared in the previous steps, such that said microorganisms ferment the cereals and generate an aqueous suspension containing (i) fermented cereal suspension and (ii) macroencapsulated immobilized probiotic or non-probiotic microorganisms;
   separating the aqueous suspension generated in the previous step from the macroencapsulated immobilized probiotic or non-probiotic microorganisms, to obtain an aqueous fermented cereal suspension without the macroencapsulated immobilized probiotic or non-probiotic microorganisms; and
   incorporating into the aqueous fermented cereal suspension without the macroencapsulated immobilized probiotic or non-probiotic microorganisms obtained in the previous step, at least one other component selected from the group consisting of:
      free or encapsulated prebiotics;
      free or microencapsulated probiotic or non-probiotic microorganisms; and
      other food ingredients, free or encapsulated.

2. The process of obtaining a fermented cereal product according to claim 1, wherein the cereals are flakes, bran or flour.

3. The process of obtaining a fermented cereal product according to claim 1, wherein the cereals include oats.

4. The process of obtaining a fermented cereal product according to claim 1, wherein the cereals are combined with at least one of the following elements:
   one or more other cereals applied in food industry; or
   one or more legumes.

5. The process of obtaining a fermented cereal product according to claim 1, wherein in the step of preparing the cereal suspension the water used therein is previously obtained through an osmosis process in order to remove minerals that cause off-flavours in the water.

6. The process of obtaining a fermented cereal product according to claim 1, wherein the step of preparing the cereal suspension is carried out until a sugar content, in terms of glucose, is at least 150 g/L and at least 25±5° Brix.

7. The process of obtaining a fermented cereal product according to claim 1, wherein the α-amylase is used on a concentration between 0.01% and 2% of cereal concentration, glucoamylase is used on a concentration between 0.01% and 1% of cereal concentration and glutaminase is used on a concentration between 0.01% and 1% of cereal concentration.

8. The process of obtaining a fermented cereal product according to claim 1, wherein the macroencapsulated immobilized probiotic or non-probiotic microorganisms are generally recognized as safe.

9. The process of obtaining a fermented cereal product according to claim 1, wherein the macroencapsulated immobilized probiotic or non-probiotic microorganisms are from the *Bifidobacterium* or *Lactobacillus* genera.

10. The process of obtaining a fermented cereal product according to claim 1, wherein the amount of free or microencapsulated probiotic or non-probiotic microorganisms incorporated into the above-described fermented cereal suspension is at least $10^8$-$10^{10}$ CFU/g.

11. The process of obtaining a fermented cereal product according to claim 1, wherein the macroencapsulated immobilized probiotic or non-probiotic microorganisms are encapsulated in a coating material selected from proteins, polysaccharides, lipids or hydrocolloids.

12. The process of obtaining a fermented cereal product according to claim 1, wherein in the step of adding macroencapsulated immobilized probiotic or non-probiotic microorganisms to the cereal suspension prepared in the previous steps, such that said microorganisms ferment the cereals, is carried out by cereal suspension in a reactor with macroencapsulated immobilized probiotic or non-probiotic microorganisms.

13. The process of obtaining a fermented cereal product according to claim 1, wherein the soluble salt is sodium bicarbonate or sodium hydroxide.

14. The process of obtaining a fermented cereal product according to claim 1, wherein in the step of preparing capsules, the salt solution is KCl or $Ca_2Cl$.

* * * * *